United States Patent [19]

Zecher et al.

[11] 4,384,122

[45] May 17, 1983

[54] PROCESS FOR THE PRODUCTION OF IMIDAZOLIDINE TRIONES

[75] Inventors: Wilfried Zecher; Rudolf Merten, both of Leverkusen, Fed. Rep. of Germany

[73] Assignee: Bayer Aktiengesellschaft, Leverkusen, Fed. Rep. of Germany

[21] Appl. No.: 278,641

[22] Filed: Jun. 29, 1981

[30] Foreign Application Priority Data

Jul. 21, 1980 [DE] Fed. Rep. of Germany ....... 3027618

[51] Int. Cl.$^3$ .......................................... C07D 233/96
[52] U.S. Cl. .................................................. 548/307
[58] Field of Search ......................................... 548/307

[56] References Cited

U.S. PATENT DOCUMENTS 3,818,031  6/1974  Baerlocher et al. ............... 548/307
3,928,376 12/1975  Reese et al. ......................... 548/307

FOREIGN PATENT DOCUMENTS 2149713  3/1973  France .

Primary Examiner—Richard A. Schwartz
Attorney, Agent, or Firm—Connolly and Hutz

[57] ABSTRACT

A process for the production of imidazolidine triones by reacting optionally masked iso(thio)cyanates with oxalic acid mono esters.

5 Claims, No Drawings

PROCESS FOR THE PRODUCTION OF IMIDAZOLIDINE TRIONES

It is known that imidazolidine triones are obtained by reacting 1,3-diprimary ureas with oxalyl chloride (Chem. Ber. 46, 1387). Other production methods include the cyclization of isocyanates with hydrocyanic acid with subsequent hydrolysis of the resulting imino compounds (Makromol. Chem. 78, 186 and U.S. Pat. No. 3,661,859) and the reaction of oxamic acid esters with isocyanates (German Auslegeschrift No. 1,770,146). Monomolecular substituted imidazolidine triones may be used in the pharmaceutical field and for plant protection, while polyimidazolidine triones have become particularly significant as temperature-resistant plastics.

It has now been found that imidazolidine triones are obtained in good yields when organic iso(thio)cyanates or corresponding masked iso(thio)cyanate are reacted with oxalic acid monoesters at temperatures of from 0° to 450° C., preferably from 30° to 150° C.

The course of the reaction is surprising, because isocyanates and carboxylic acids, usually react to form predominantly the corresponding ureas and acid anhydrides which may then react with further isocyanate to form complicated substance mixtures. Oxalic acid monoesters also decompose at relatively low temperatures with release of carbon dioxide so that a condensation reaction could not be foreseen. The starting materials are easily accessible and may be purified by simple distillation. The relatively good yields of imidazolidine triones which facilitate polymer construction could not be expected in the reaction of the invention which takes place during several stages. Only carbon dioxide and alcohol are released as by-products in the polycondensation process.

The oxalic acid monoesters used as starting materials according to the invention are obtainable, for example, from oxalic acid by partial esterification or from oxalic acid diesters by partial hydrolysis and may be introduced as such or they may also be produced from the components in the reaction medium. Compounds of the following general formula are preferably used:

$$R_1(OOCCOOH)_n$$

wherein
$R_1$ represents an optionally substituted, aliphatic radical preferably having 1 to 22 carbon atoms, particularly preferably 1 to 6 carbon atoms, an aliphatic-aromatic radical preferably having 7 to 20 carbon atoms, particularly preferably 7 to 10 carbon atoms, or an aromatic radical, preferably having 5 to 10 carbon atoms, particularly preferably 6 to 10 carbon atoms, a heterocyclic radical, preferably having 3 to 10 ring carbon atoms and from 1 to 3 hetero atoms, such as N, S and/or O in the ring or a polyether, polyester or polyurethane radical,
and n represents an integer from 1 to 3, preferably 1.
The radical $R_1$ is preferably derived from methane, ethane, n-, iso- or tert.-butane, hexane, eicosane, propene, butine, cyclohexane, benzene, naphthalene, diphenyl methane or nuclear-substituted toluene and xylene. The radical $R_1$ may be substituted one or more times with halogen atoms, $C_1$–$C_6$ alkyl or $C_6$–$C_{10}$ aryl radicals, carboxylic acid or carboxylic acid ester groups.

The $C_1$–$C_6$ monoesters of oxalic acid with monofunctional aliphatic alcohols are particularly preferably used.

Aliphatic and aromatic compounds optionally substituted by hetero atoms, with an NCO group in the molecule are used as organic monoisocyanates in the context of this invention, e.g. alkyl isocyanates such as ethyl-, methyl-, butyl-, dodecyl- and stearylisocyanate, aromatic, optionally substituted monoisocyanates, such as phenyl-, tolyl-, isopropyl-, nonylisocyanate, nitro-, alkoxy-, aroxy-, chloro-, dichloro-, trichloro-, tetra-, pentachloro-, benzyl-, bromo-phenyl-isocyanate, or isocyanatobenzoic acid ester, phthalic acid ester, isophthalic acid ester, isocyanatobenzonitrile, cycloaliphatic isocyanates such as cyclohexylisocyanate and unsaturated isocyanates such as allyl-, oleyl- and cyclohexenyl-isocyanate.

Aliphatic, cycloaliphatic, araliphatic, aromatic and heterocyclic polyisocyanates, preferably diisocyanates, are also included as starting components to be used according to the invention (see Annalen, 562, pages 75 to 136), for example ethylene diisocyanate, 1,4-tetramethylenediisocyanate, 1,6-hexamethylene-diisocyanate, 1,12-dodecanediisocyanate, cyclobutane-1,3-diisocyanate, cyclohexane-1,3 and -1,4 diisocyanate and any mixtures of these isomers; 1-isocyanato-3,3,5-trimethyl-5-isocyanatomethyl-cyclohexane (German Auslegeschrift No. 1,202,785), 2,4- and 2,6-hexahydrotoluylenediisocyanate and any mixtures of these isomers; hexahydro-1,3- and/or -1,4-phenylenediisocyanate, perhydro-2,4' and/or -4,4'-diphenylmethane-diisocyanate, 1,3- and 1,4-phenylene-diisocyanate, 2,4- and 2,6-toluylene-diisocyanate and any mixtures of these isomers; diphenylmethane-2,4'- and/or -4,4'-diisocyanate; naphthylene-1,5-diisocyanate; triphenylmethane-4,4',4"-triisocyanate; polyphenyl-polymethylenepolyisocyanates as obtained by aniline-formaldehyde-condensation and subsequent phosgenation and described, for example, in British Pat. Nos. 874,430 and 848,671; perchlorinated arylpolyisocyanates as described, for example, in German Auslegeschrift No. 1,157,601; polyisocyanates having carbodiimide groups as described in German Pat. No. 1,092,007; diisocyanates as described in U.S. Pat. No. 3,492,330; polyisocyanates having allophanate groups as described, for example, in British Pat. No. 99,800, in Belgian Pat. No. 761,626 and in published Dutch Patent application No. 7,102,524; polyisocyanates having isocyanurate groups, as described, for example, in German Pat. Nos. 1,022,789; 1,222,067 and 1,027,394 and in German Offenlegungsschriften Nos. 1,929,034 and 2,004,048; polyisocyanates having urethane groups, as described, for example, in Belgian Pat. No. 752,261 or in U.S. Pat. No. 3,394,164; polyisocyanates having acylated urea groups according to German Pat. No. 1,230,778; polyisocyanates having biuret groups, as described, for example, in German Pat. No. 1,101,394, in British Pat. No. 889,050 and in French Pat. No. 7,017,514; polyisocyanates produced by a telomerisation reaction, as described, for example, in Belgian Pat. No. 723,640; polyisocyanates having ester groups, as described, for example, in British Pat. Nos. 956,474 and 1,072,956, in U.S. Pat. No. 3,567,763 and in German Pat. No. 1,231,688 and reaction products of the above-mentioned isocyanates with acetylene according to German Pat. No. 1,072,358.

It is also possible to use the distillation residues having isocyanate groups and resulting from the commercial isocyanate production, optionally dissolved in one or more of the previously mentioned polyisocyanates. Furthermore, it is possible to use any mixtures of the polyisocyanates mentioned above.

Mono- or poly-iso(thio)cyanates of the following general formula are particularly suitable:

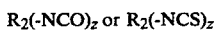

$R_2(-NCO)_z$ or $R_2(-NCS)_z$ wherein $R_2$ represents an aliphatic radical having from 1 to 20 carbon atoms and optionally substituted with halogen, C-C alkyl and/or aryl $C_6$-C groups, an aromatic radical having from 5 to 12 carbon atoms, a cycloaliphatic radical having from 5 to 12 carbon atoms, an aliphatic-aromatic radical having from 6 to 20 carbon atoms and an aromatic or cycloaliphatic radical having from 5 to 12 carbon ring atoms containing hetero atoms such as N, O or S in the ring. Aliphatic radicals having from 2 to 12 carbon atoms are particularly preferred, or an aryl radical such as phenyl, tolyl, naphthyl, diphenyl methane and diphenyl ether radicals. z is an integer from 1 to 4, preferably from 1 to 3 and particularly preferably 2.

The following are preferably used: the commercially readily available mixtures from toluylene-diisocyanates, m-phenylene diisocyanate, phenyl isocyanate and the substitution products thereof, methyl isocyanate and phosgenated condensates from aniline and formaldehyde with a polyphenylene methylene structure and the symmetrical compounds 4,4'-diisocyanato-diphenyl methane, 4,4'-diisocyanato-diphenyl ether, p-phenyl diisocyanate, 4,4'-diisocyanato-diphenyl-dimethyl methane, analogous hydroaromatic diisocyanates and aliphatic diisocyanates having from 2 to 12 carbon atoms, such as hexamethylene diisocyanate and diisocyanates derived from isophorone.

The isocyanates may be used in the free form or partly or completely in the masked form which act as a donor under the reaction conditions and which are available upon reacting with compounds containing reactive hydrogen.

Preferably used as donors are the acyl-ureas available from lactams, e.g. caprolactam, and the carbamic acid esters obtained from aromatic and aliphatic mono- and poly-hydroxy compounds, corresponding, for example, to the general formulae;

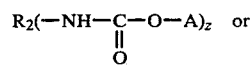

$R_2(-NH-\underset{\underset{O}{\|}}{C}-O-A)_z$ or

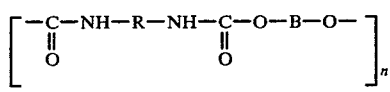

$$\left[ -\underset{\underset{O}{\|}}{C}-NH-R-NH-\underset{\underset{O}{\|}}{C}-O-B-O- \right]_n$$

wherein $R_2$ and z are represented as above and A is the organic radical of a monohydroxy compound or B is the organic radical of a bis- or tris-functional hydroxy compound, preferably an aliphatic radical having from 1 to 10 carbon atoms, a cycloaliphatic radical having from 5 to 10 carbon atoms, an aliphatic-aromatic radical having from 7 to 12 carbon atoms and an aromatic radical having from 6 to 12 carbon atoms which radicals may also be substituted with alkyl and/or aryl groups, and n represents an integer from 1 to 1000, preferable from 1 to 100.

The following are mentioned as examples: the carbamic acid esters from phenol, isomeric cresols, the commercial mixtures thereof and similar aromatic hydroxyl compounds, aliphatic monoalcohols such as methanol, ethanol, propanol, isopropanol, butanol; isobutanol, diethyleneglycolmonomethylether, cyclohexanol, benzyl alcohol and aliphatic di- or polyols such as ethyleneglycol and trimethylolpropane.

The urethanes may be used as such or may be produced in situ by reaction with alcohols.

The analogous (poly)isothiocyanates may be used instead of the (poly)isocyanates mentioned.

The reaction according to the invention can be explained by the following reaction diagram:

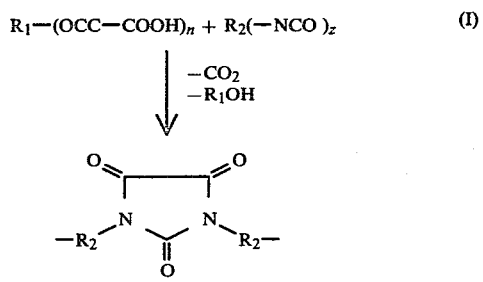

$$R_1-(OCC-COOH)_n + R_2(-NCO)_z \quad (I)$$
$$\downarrow \begin{array}{c} -CO_2 \\ -R_1OH \end{array}$$

wherein the radicals $R_1$ and $R_2$ are represented as above. Where $z=1$, a monomolecular compound is produced and where $z>1$, a higher molecular compound is produced with the recurring structural unit (I), whereby the imidazolidine trione rings are linked via the radicals $R_2$.

The imidazolidine triones according to the invention may be identified by IR-spectra, in which the characteristic bands for imidazolidine triones occur. The higher-molecular-weight imidazolidine triones exhibit a solution viscosity of from 100 to 200,000 mPa.s, preferably from 1,000 to 50,000, which is determined in a 30% solution in e.g. N-methylpyrrolidone at 25° C.

The reaction of the invention may be carried out in solvents which do not react under the reaction conditions or only form loose addition compounds or also in an excess of one of the reaction components. Suitable solvents are the following: hydrocarbons, phenols, alcohols, esters, lactones, ketones, ethers, substituted amides, nitriles, phosphoric acid amides, sulphoxides and sulphones which may be optionally substituted by halogen, for example xylenes, o-dichlorobenzene, phenol, cresols, benzoicacidalkylester, phthalic acid dimethylester, butyrolactone, caprolactone, acetophenone, cyclohexanone, benzylalcohol, ethylene glycol, glycol monomethyletheracetate, diethyleneglycolmonoethylether, diethyleneglycol dimethylether, dimethylformamide, N-methylpyrrolidone, caprolactam, benzonitrile, hexamethylphosphoric acid triamide, dimethylsulphoxide, tetramethylenesulphone and their mixtures.

The present process is preferably carried out such that the reaction components are maintained for a few minutes up to several hours at temperatures of approximately from 0° to 450° C., preferably from 30° to 150° C., either in the presence or absence of a solvent. The course of the reaction takes place with evolution of gas, the release of the alcohol being shown by the IR spectra. Occasionally, it is advantageous to carry out the reaction in several stages or to add the individual components in a varying sequence or at different temperatures. Particularly in the production of polymers, a condensation product may be produced in a first stage, for example in a solvent, which product is then converted into the high-molecular-weight reaction product, e.g. a lacquer film, at elevated temperatures with chain-lengthening or cross-linking and optionally with evaporation of the solvent. For use as lacquers, the products may also be formed from melts or aqueous dispersions.

In general 2 val of isocyanate are used per val of oxalic acid mono ester. However, very extensive deviations from these proportions are also possible. Monomolecular imidazolidine triones are obtained from monoesters and monofunctional isocyanates and higher-molecular-weight imidazolidine triones or oligomers, like imidazolidine-isocyanates or imidazolidine-urethanes are obtained from monoesters and polyisocyanates, depending on the stoichiometric ratios.

Another embodiment of the present reaction for the production of a polymer comprises carrying out the condensation process in the presence of polyalcohols, polyamines, polycarboxylic acids, polycarboxylic acid anhydrides and/or excess polyisocyanates or a combination thereof, such as amino alcohols or amino carboxylic acids. Thus, polyimidazolidine trione ester is obtained using terephthalic acid and ethylene glycol and polyimidazolidine trione-amide-imides are obtained using trimellitic acid anhydride and diisocyanates.

The reaction according to the invention may be accelerated by using conventional isocyanate catalysts, like amines such as triethylamine, 1,4-diazabicyclo-(2,2,2)-octane, N-ethyl-morpholine, N-methylimidazole, 4-dimethylamino-pyridine, and 4-(1-pyrolidino)-pyridine, and by organic and inorganic metal compounds, in particular compounds of iron, lead, zinc, tin copper, cobalt and titanium, such as iron-(III)-chloride, cobalt acetate, lead oxide, lead acetate, tin octoate, dibutyl-tin-dilaurate, copper-acetyl-acetonate, titanium tetrabutylate, alkali-phenolates and sodium cyanide and by phosphorus compounds such as trialkyl phosphine and methyl phospholine oxide and hydroxy aromatic compounds such as phenol, hydroquinone and resorcinol.

The monomolecular imidazolidine triones which may be produced according to the present process are effective in the pharmaceutical and plant protection sectors. The present polyimidazolidine triones are distinguished by a particularly good temperature-resistance and are suitable for use as adhesives, lacquers, films and moulded bodies. Their characteristics may be varied within wide limits for the various areas of use by adding fillers, pigments and low and high-molecular-weight components, for example by mixing with polyesters and polycarbamic esters for the production of lacquers and films.

EXAMPLE 1

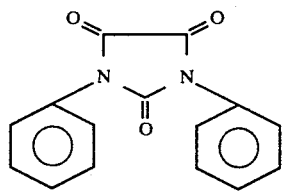

59 g of oxalic acid monoethylester, 179 g of phenyl isocyanate and 0.2 g of triethylene diamine are introduced into 240 g of N-methylpyrrolidone. The mixture is then heated with stirring to 80° C. for 4 hours and then further heated for 2 hours at 100° C. and for 2 hours at 120° C. Condensation and subsequent cyclization take place with carbon dioxide and ethanol splitting off. The reaction product is precipitated with water and the precipitation is stirred with methanol for separating N-phenyl carbamic acidethylester. 102 g (78% of the theoretical yield) of 1,3-diphenylimidazolidine -2,4,5-trione with a melting point of from 190° to 197° C. is obtained as a residue after filtering with suction. The material is taken up in acetonitrile for purification, is filtered, evaporated and the residue is recrystallised from toluene. The resulting pure compound is obtained as colourless polyhedra with a melting point of from 205° to 206° C. and a characteristic band in the IR spectrum at 1750 cm$^{-1}$.

$C_{15}H_{10}N_2O_3$ (266): Calculated: C 67.7; H 3.8; N 10.5%. Found: C 67.6; H 3.8; N 10.7%.

EXAMPLE 2

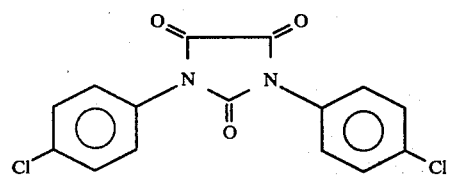

26 g of oxalic acid monomethylester and 77 g of 4-chlorophenyl isocyanate are dissolved in 200 g of butyrolactone. The temperature is then slowly increased to 120° C. and the mixture is stirred for 6 hours at 120° C. and for a further 2 hours at 140° C. The reaction into the imidazolidine-trione takes place with carbon dioxide and methanol splitting off. When the reaction has finished, the reaction mixture is mixed with water and the precipitate is taken up in acetone, filtered and the filtrate is evaporated. When recrystallised from acetonitrile, the evaporation residue produces 1,3-bis-(4-chlorophenyl)-imidazolidine-trione as colourless polyhedra with a melting point of from 275° to 258° C. and a band at 1740 cm$^{-1}$.

$C_{15}H_8Cl_2N_2O_3$ (355): Calculated: C 53.7; H 2.4; N 8.4%. Found: C 53.8; H 2.4; N 8.6%.

EXAMPLE 3

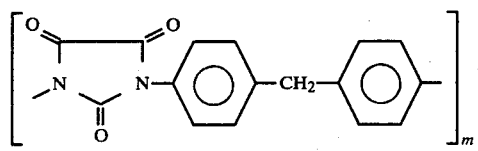

59 g of oxalic acid monoethylester and 130 g of 4,4'-diisocyanatophenylmethane are introduced into 320 g of N-methylpyrrolidone. The mixture is then stirred for 4 hours at 80° C. and the temperature is then increased 20° C. every two hours up to a temperature of 200° C. The mixture is then stirred for a further 4 hours at this temperature. The polyimidazolidine-trione is obtained with the recurring structural unit specified, as a clear brown solution with a viscosity of 560 mPas and a band at 1750 cm$^{-1}$ which is characteristic of imidazolidine triones.

A sample of the solution is coated onto a glass plate and is stoved to a clear elastic film for 15 minutes at both 200° C. and 300° C. The polyimidazolidine trione is precipitated with water as a yellowish-brown powder from another sample.

$(C_{16}H_{10}N_2O_3)_n$ $(278)_n$: Calculated: C 69.1; H 3.6; N 10.1%. Found: C 69.3; H 4.0; N 10.5%.

EXAMPLE 4

The reaction is carried out as described in Example 3 using 320 g of a commercial cresol mixture as the solvent. The poly-imidaziline-trione is obtained as a brown viscous solution which is stoved to a clear elastic lacquer film on a tin foil for 15 minutes at both 200° C. and 300° C. The IR spectrum contains the band at 1750 cm$^{-1}$ which is characteristic of imidazolidine triones.

EXAMPLE 5

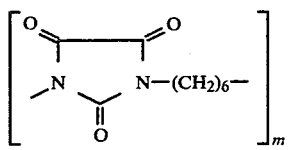

26.0 g of oxalic acid monomethylester and 43.7 g of hexamethylenediisocyanate are dissolved in 120 g of dimethylacetamide and the mixture is then heated for 4 hours at each temperature 80°, 120°, 130°, 140° and 150° C. The polyimidazolidine trione is obtained with the recurring structural unit specified, as a brown viscous solution, from which a sample is stoved to a clear hard lacquer film on a mirror sheet for 15 minutes at both 200° C. and 300° C. The IR spectrum contains a band at 1750 cm$^{-1}$ which is characteristic of imidazolidine trione.

EXAMPLE 6

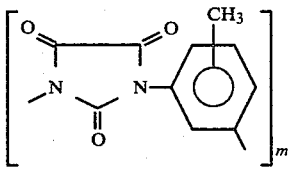

61 g of oxalic acid mono isopropylester and 90.5 g of a commercial mixture of 80%, 2,4- and 20% 2,6-toluylene diisocyanate are dissolved in 260 g of butyrolactone. The mixture is then stirred for 4 hours at each temperature 80°, 120°, 140° and 150° C. 0.3 g Of triethylene diamine are added and the mixture is heated for another 10 hours at 150° C. to complete the reaction. The polyimidazolidine-trione is obtained with the recurring structural unit specified, as a brown viscous solution.

A sample of the solution is stoved to a clear hard lacquer film on a mirror sheet at 200° C. and 300° C. and the film exhibits a characteristic band at 1755 cm$^{-1}$ in the IR spectrum.

The polyimidazolidinetrione is precipitated as a yellow powder with a band at 1755 cm$^{-1}$ from another sample.

EXAMPLE 7

Poly-amide-imide-triazolidine trione.

29.6 g of oxalic acid monoethylester, 48.0 g of trimellitic acid anhydride and 130 g of 4,4'-diisocyanatodiphenyl methane are introduced into 370 g of N-methylpyrrolidone. The mixture is then heated with stirring for 4 hours each of the temperatures 80°, 120°, 140° and 150° C. Condensation takes place with carbon dioxide and ethanol splitting off. The poly-amide-imide-triazolidinetrione is obtained as a clear brown solution with a viscosity $\eta$ 25=360 mPas.

The polycondensate is precipitated from a sample of this solution as a yellow powder, which exhibits bands characteristic of amides at 1670 cm$^{-1}$, of imidazolidine triones at 1750 cm$^{-1}$ and of imides at 1720 and 1780 cm$^{-1}$.

Another sample of the lacquer solution is stoved to a clear elastic lacquer film on a glass plate at 200° C. and 300° C. A mixture of cresol and phenol as the solvent may also be used instead of N-methylpyrrolidone.

We claim:

1. A process for producing a compound containing at least one imidazolidine-trione structure in the molecule which comprises reacting at least one organic iso(thio)-cyanate or at least one masked iso(thio)cyanate whose masking groups are removable under the reaction conditions specified below, with an oxalic acid mono ester at a temperature of from 0° to 450° C.

2. The process of claim 1 wherein said oxalic acid mono ester is of the formula $$R_1(OOCCOOH)_n$$

wherein $R_1$ is an aliphatic radical having 1 to 22 carbon atoms, an aliphatic-aromatic radical having 7 to 20 carbon atoms, an aromatic radical having 5 to 10 carbon atoms, a heterocyclic radical having 3 to 10 ring carbon atoms and from 1 to 3 hetero atoms, a polyether radical, a polyester radical, a polyurethane radical or one of said radicals substituted at least once with halogen, $C_1$-$C_6$ alkyl, $C_6$-$C_{10}$ aryl, carboxy or an esterified carboxy group and n is an integer of from 1 to 3.

3. The process of claim 2 wherein $R_1$ is a $C_1$-$C_6$ aliphatic radical, a $C_7$-$C_{10}$ aliphatic-aromatic radical, a $C_6$-$C_{10}$ aromatic radical or one of said radicals substituted at least once with halogen, $C_1$-$C_6$ alkyl, $C_6$-$C_{10}$ aryl, carboxy or an esterified carboxy group and n is 1.

4. The process of claim 1 wherein said oxalic acid mono ester is a $C_1$-$C_6$ alkyl mono ester of oxalic acid.

5. The process of claim 1 wherein at least one polyiso(thio)cyanate is used.

* * * * *